(12) United States Patent
Zhang et al.

(10) Patent No.: US 10,495,593 B2
(45) Date of Patent: Dec. 3, 2019

(54) TESTING METHOD FOR SHEET RESISTANCE OF SHEET MATERIAL

(71) Applicant: SHANGHAI INSTITUTE OF CERAMICS, CHINESE ACADEMY OF SCIENCES, Shanghai (CN)

(72) Inventors: Bufa Zhang, Shanghai (CN); Lixin Song, Shanghai (CN)

(73) Assignee: SHANGHAI INSTITUTE OF CERAMICS, CHINESE ACADEMY OF SCIENCES, Shanghai (CN)

( * ) Notice: Subject to any disclaimer, the term of this patent is extended or adjusted under 35 U.S.C. 154(b) by 27 days.

(21) Appl. No.: 15/763,961

(22) PCT Filed: Sep. 28, 2016

(86) PCT No.: PCT/CN2016/100569
§ 371 (c)(1),
(2) Date: Mar. 28, 2018

(87) PCT Pub. No.: WO2017/054730
PCT Pub. Date: Apr. 6, 2017

(65) Prior Publication Data
US 2018/0284046 A1    Oct. 4, 2018

(30) Foreign Application Priority Data
Sep. 29, 2015  (CN) .......................... 2015 1 0638358

(51) Int. Cl.
*G01N 27/04*    (2006.01)
(52) U.S. Cl.
CPC .................................. *G01N 27/041* (2013.01)
(58) Field of Classification Search
CPC ...... G01N 27/041; G01N 17/02; G01R 27/14; G01R 27/025
(Continued)

(56) References Cited

U.S. PATENT DOCUMENTS 5,184,398 A * 2/1993 Moslehi .............. C23C 16/4583
257/E21.531
2005/0052191 A1 3/2005 Prussin
(Continued)

FOREIGN PATENT DOCUMENTS

CN    101666829 A    3/2010
CN    103884912 A    6/2014
(Continued)

OTHER PUBLICATIONS

Chinese National Standard "GB/T 14141-2009 Test Method for Sheet Resistance of Silicon Epitaxial, Diffused and Ion-Implanted Layers Using a Collinear Four-Probe Array", which published on Oct. 30, 2009, 10 pages.
(Continued)

*Primary Examiner* — Melissa J Koval
*Assistant Examiner* — Trung Nguyen
(74) *Attorney, Agent, or Firm* — Alleman Hall Creasman & Tuttle LLP

(57) ABSTRACT

A testing method for the sheet resistance of a sheet material, comprising: mounting two circular or annular electrodes on the surface of the sheet material; measuring the resistance between the electrodes; and calculating the sheet resistance of the sheet material on the basis of a theoretical model from the resistance measured between the electrodes, the diameters of the electrodes, and the distance between the electrodes. The method places no restriction on the diameters of the electrodes; also, the annular electrodes work as effectively as circular electrodes, and annular electrodes may improve the contact between the edges of the electrodes, and the sheet material.

12 Claims, 3 Drawing Sheets

(58) Field of Classification Search
USPC .......... 324/600, 691–693; 200/207.21, 252, 200/500, 525, 549, 727
See application file for complete search history.

(56) References Cited

U.S. PATENT DOCUMENTS

| | | |
|---|---|---|
| 2009/0128167 A1 | 5/2009 | Hamada et al. |
| 2015/0260670 A1* | 9/2015 | Shu .................. G01N 27/041 |
| | | 324/693 |

FOREIGN PATENT DOCUMENTS

| | | |
|---|---|---|
| CN | 105182081 A | 12/2015 |
| CN | 105203847 A | 12/2015 |

OTHER PUBLICATIONS

Chinese National Standard "GB/T 1410-2006 Methods of Test for Volume Resistivity and Surface Resistivity of Solid Electrical Insulating Materials", which published on Feb. 15, 2006, 18 pages.
ISA State Intellectual Property Office of the People's Republic of China, International Search Report issued in PCT Application No. PCT/CN2016/100569, Nov. 30, 2016, WIPO, 4 pages. (Submitted with English Translation of Search Report).

\* cited by examiner $$V(x,y) = \frac{I_0 R_\square}{4\pi} \ln\left[\frac{\left(x+\frac{L_0}{2}\right)^2+y^2}{\left(x-\frac{L_0}{2}\right)^2+y^2}\right] \quad (1)$$

$$L_A = \frac{1}{2L_{AB}}\left[L_{AB}^2 + r_A^2 - r_B^2 - \sqrt{(L_{AB}^2 - r_A^2 - r_B^2)^2 - 4r_A^2 r_B^2}\right] \quad (2)$$

$$L_B = \frac{1}{2L_{AB}}\left[L_{AB}^2 + r_A^2 - r_B^2 + \sqrt{(L_{AB}^2 - r_A^2 - r_B^2)^2 - 4r_A^2 r_B^2}\right] \quad (3)$$

$$\vec{q} = \frac{I_0}{2\pi t}\left[\frac{x-\frac{L_0}{2}}{\left(x-\frac{L_0}{2}\right)^2+y^2} - \frac{x+\frac{L_0}{2}}{\left(x+\frac{L_0}{2}\right)^2+y^2}\right]\vec{\imath}$$
$$+ \frac{I_0}{2\pi t}\left[\frac{y}{\left(x-\frac{L_0}{2}\right)^2+y^2} - \frac{y}{\left(x+\frac{L_0}{2}\right)^2+y^2}\right]\vec{\jmath} \quad (4)$$

$$x^2 + \left(y + \frac{L_0}{2\tan\theta}\right)^2 = \left(\frac{L_0}{2\sin\theta}\right)^2 \quad (5)$$

$$R_{AB} = \frac{R_\square}{2\pi}\ln\left[\frac{L_{AB}^2 - r_A^2 - r_B^2}{2r_A r_B} + \sqrt{\left(\frac{L_{AB}^2 - r_A^2 - r_B^2}{2r_A r_B}\right)^2 - 1}\right] \quad (6)$$

$$R_\square = \frac{2\pi R_{AB}}{\ln\left[\frac{L_{AB}^2 - r_A^2 - r_B^2}{2r_A r_B} + \sqrt{\left(\frac{L_{AB}^2 - r_A^2 - r_B^2}{2r_A r_B}\right)^2 - 1}\right]} \quad (7)$$

FIG. 3

TESTING METHOD FOR SHEET RESISTANCE OF SHEET MATERIAL

FIELD OF THE INVENTION

The present invention relates to a testing method for sheet resistance of electrically conductive sheet materials. The sheet materials include monolayer or multilayer conductive materials, may be metal materials, alloy materials, semiconductor materials, coatings, and thin film materials, and may be stand-alone or supported by a non-conductive substrate.

BACKGROUND OF THE INVENTION

Sheet resistance is one of the important properties of a sheet material, the precise measurement of which is an important means to assess and monitor a semiconductor material. Meanwhile sheet materials are widely used in the fabrication of electronic components, and the sheet resistance performance thereof directly affects the quality of the component. Sheets of metal materials, alloy materials, and semiconductor materials, and electrically conductive coating materials on a substrate are applied to the semiconductor component fabrication and electronic circuit connection, as well as the surface modification and protection of objects.

The current Chinese National Standard "GB/T 14141-2009 TEST METHOD FOR SHEET RESISTANCE OF SILICON EPITAXIAL, DIFFUSED AND ION-IMPLANTED LAYERS USING A COLLINEAR FOUR-PROBE ARRAY" has made detailed requirements on the four-probe method for testing the sheet resistance of semiconductor materials, that the probe tip should have a hemispherical shape (with a radius of 35 µm-250 µm) or a flat circular section (with a radius of 50 µm-125 µm).

The potential field in the sample generated by the two terminal electrodes in the collinear four-probe array method is unavoidably affected by the two middle testing electrodes. This standard strictly requires that the distance between adjacent probes be 1.59 mm, which limits the application range of the sample. In order to avoid the impact of electric heating of small contact point of probes on the measuring surface, the probe current should be controlled to less than 100 mA. In addition, the shape of the indentation by the probe on the surface of the tested material is difficult to control, and thus repeated testing is required to ensure the reliability of measurement results, as well as to improve the measurement accuracy. In short, the process using the collinear four-probe array method for measuring the sheet resistance of a sheet material is complicated, and demanding on the measurement instruments and operation skills, which limits its application.

For solid electrical insulating materials, the Chinese National Standard "GB/T 1410-2006 METHODS OF TEST FOR VOLUME RESISTIVITY AND SURFACE RESISTIVITY OF SOLID ELECTRICAL INSULATING MATERIALS" specifies the measurement procedures and calculation methods for testing surface resistivity of plate materials using concentric ring electrodes.

SUMMARY OF THE INVENTION

In view of the above disadvantages presented in the prior art, the technical problem to be solved by the present application is to provide a testing method for sheet resistance of sheet materials, by which the above difficulties existing in the prior art can be overcome, and the electrode diameter is not limited, thus the contact resistance of electrode/substrate interface and the electric heating effect on the sample surface can be reduced by increasing the electrode diameter.

In order to solve the above-mentioned technical problems, the present application provides a testing method for sheet resistance of a sheet material, comprising: mounting two circular or annular electrodes on the surface of the sheet material; measuring the resistance between the electrodes; and calculating the sheet resistance of the sheet material on the basis of a theoretical model from the resistance measured between the electrodes, the diameter of each electrode, and the distance between the electrodes.

According to the present application, the distribution of the potential and the electric current generated in the sheet material when direct current runs through the pair of circular or annular electrodes is calculated. At the same time, a method for calculating the resistance of the sheet material between the pair of electrodes is provided, and then the sheet resistance of the sheet material is determined by measuring this resistance. In the method of the present application, the diameters of the electrodes are not limited, and the annular electrode may work as effectively as the circular electrode in the measurement. Furthermore, the use of the annular electrode may improve the contact between the electrode's edge and the sheet material.

Further, in the present application, the sheet material under testing may be an electrical conductive material, including metal material, alloy material, semiconductor material, coating, or film material. In addition, the sheet material may include monolayer material or multilayer material, and the sheet material may be stand-alone or supported by a non-conductive substrate.

Further, in the present application, the electrode may be the connection means between the sheet material and a circuit, and the electrode may be connected to the sheet material by pressure-contact, gluing, soldering, or electric welding of the surface of the conductor.

Further, in the present application, the thickness of sheet material under testing may be uniform, preferably with an unevenness of less than 1%; and wherein the thickness of the sheet material is much less than the diameters of the electrodes, preferably less than ⅒ of the smaller diameter of the two electrodes.

According to the present application, the distribution of potential and electric current in the sheet material generated when direct current passes through the circular electrode pair is uniform in the depth direction of the material, and the theoretical analysis thereof can be treated mathematically as a two-dimensional problem.

Further, in the present application, the planar dimensions of the sheet material may be much greater than the distance between the electrodes, preferably greater than 10 times the distance between the electrodes, wherein the planar dimensions may be the length, the width, or the diameter of the sheet material.

Further, in the present application, the distance between the electrode and the edge of the sheet material may be much greater than the distance between the electrodes, preferably greater than 5 times the distance between the electrodes.

According to the present application, the planar dimensions of the sheet material are much greater than the distance between the electrodes, and the closest distance between each electrode and the edge of the material is much greater than the distance between the electrodes. Therefore, the potential and electric current at the edge of the material are very small and the edge reflection effect can be neglected.

Further, a point source model may be used to calculate the potential and the current in the sheet material generated by the circular or annular electrodes in the present application.

Further, in the present application, it is required that the conductivity of the electrode material be much greater than that of the sheet material; therefore, the potential distribution within each of the electrodes is uniform, and it is required that the contact resistance of the electrode/sheet material interface be small. That is, as compared with the resistance of the sheet material, the resistance within the electrode and the contact resistance of the electrode/sheet material interface are required to be very small, thus being negligible in the test. Similarly, the resistance of the electrode lead is known or considered to be very small in the measurement. Therefore, during the theoretical analysis, the resistance within the electrode, the resistance of the electrode lead and the contact resistance of the electrode/substrate interface are not taken into account.

The present application can overcome the above-mentioned difficulties in the prior art, and there is no limitation on the electrode diameter, thus the contact resistance of the electrode/substrate interface and the electric heating effect on the sample surface can be reduced by increasing the electrode diameter.

The foregoing and other objects, features, and advantages of the present application will be better understood from the following detailed description and with reference to the drawings.

BRIEF DESCRIPTION OF THE DRAWINGS

FIG. 3 contains the related equations used in the present application.

Reference numbers: 1—Sheet material; 2—Electrode A (First electrode); 3—Electrode B (Second electrode); 4—Electrode leads.

DETAILED DESCRIPTION OF THE EMBODIMENTS

The present invention will be further described below with reference to the accompanying drawings and the following embodiments. It should be understood that the accompanying drawings and the following embodiments are only used for describing the present invention rather than limiting the present invention.

Figure 1:
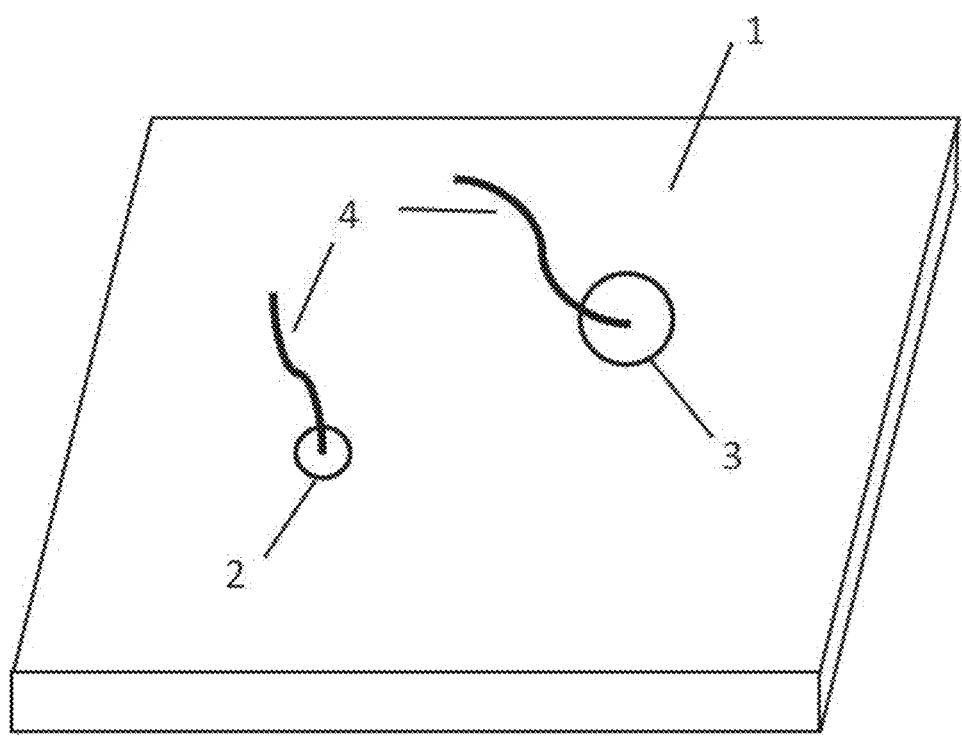
FIG. 1 is a schematic view of a method for measuring the sheet resistance of a sheet material with circular electrodes.

FIG. 1 is a schematic view of a method for measuring the sheet resistance of a sheet material with circular electrodes. Wherein the radii of electrode A as the first electrode 2 and electrode B as the second electrode 3 are $r_A$ and $r_B$, respectively, and the distance between the centers of the two electrodes is $L_{AB}$.

Figure 2:
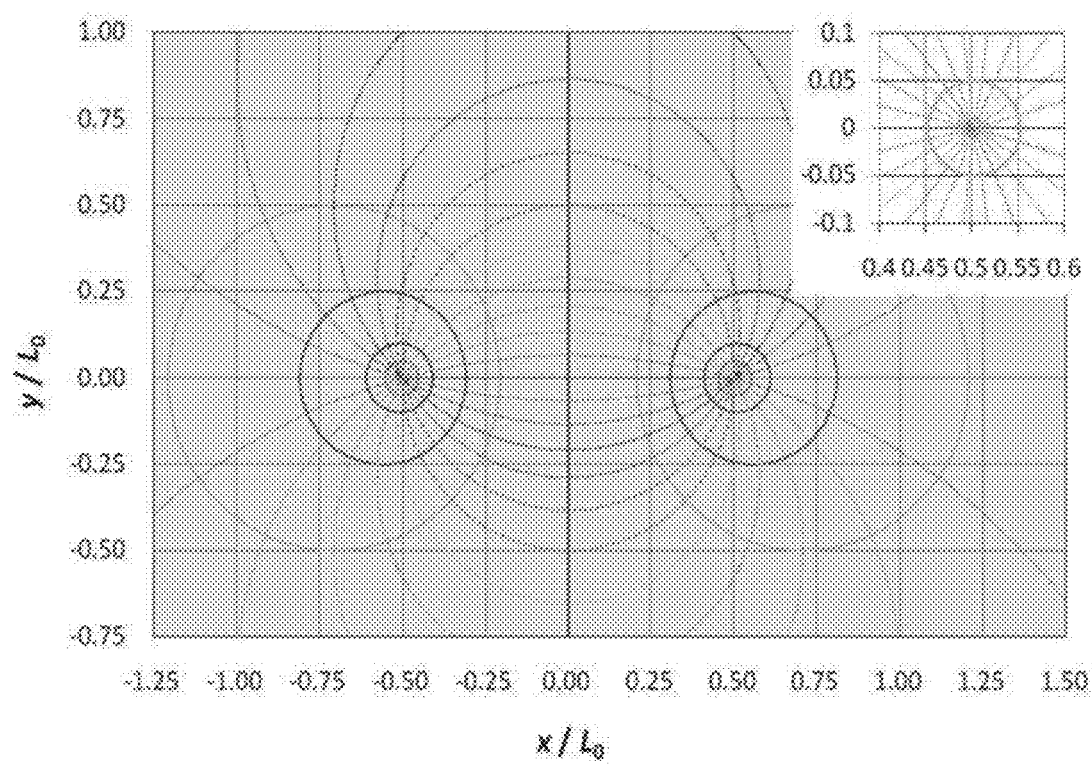
FIG. 2 is a schematic view showing the distribution of the equipotential lines and the current lines in the sheet material generated by the direct current running through two point electrodes, calculated by formulas (1) and (4).

FIG. 2 is a schematic view showing the distribution of the equipotential lines and the current lines in the sheet material generated by the direct current running through two point electrodes, calculated by equations (1) and (4). Common characteristic points of the electrodes are determined on the connecting line between the centers of two electrodes by calculation, corresponding to the locations of two common point electrodes. An appropriate coordinate system is set such that the two common points of the electrodes are located symmetrically at $(L_A/2-L_B/2, 0)$ and $(L_B/2-L_A 2, 0)$ on the x-axis. Herein, $L_A$ and $L_B$ are the distances between each of the two common electrodes and the center of electrode A (see equations (2) and (3) for the calculation of $L_A$ and $L_B$). The theoretical analysis shows that the potential and current in the sheet material outside the electrodes are the same as those generated in the sheet material by two point electrodes (with the same amount of current) at the common points of the electrodes. The solid circles around the point electrodes represent the equipotential lines, and their radii are 0.5 $L_0$, 0.25 $L_0$, 0.1 $L_0$, 0.05 $L_0$, and 0.01 $L_0$, respectively, in descending order. Herein, $L_0=L_B-L_A$ is the distance between the two common point electrodes (or point electrodes). The dotted lines represent the current lines in the sheet material, representing the paths of the currents that are emitted at angles in steps of 15° from the two point electrode positions. The density of the dotted lines represents the current intensity. The inset in FIG. 2 shows the distribution of the electric potential and the current in vicinity of the right point electrode, indicating that the closer to the point electrode, the less the centers of the equipotential circles deviate from the point electrode and the more uniform the angular distribution of the current is. According to equations (2) and (3), the center of the left equipotential circle is positioned at $-(L_A+L_2B)/2$ on the x-axis and the center of the right equipotential circle is positioned at $L_{AB}-(L_A+L_B)/2$ on the x-axis, where $L_{AB}$ is the distance between the two centers of the equipotential circles which correspond to the edge contours of the electrodes.

In view of the issues in the prior art, the present application provides a testing method for the sheet resistance of a sheet material, comprising: mounting two circular or annular electrodes on the surface of the sheet material; measuring the resistance between the electrodes; and calculating the sheet resistance of the sheet material on the basis of a theoretical model from the resistance measured between the electrodes, the diameter of each electrode, and the distance between the electrodes.

According to the present application, the distribution of the potential and the electric current generated in the sheet material when direct current runs through the pair of circular or annular electrodes is calculated. At the same time, a method for calculating the resistance of the sheet material between the pair of electrodes is provided, and then the sheet resistance of the sheet material is determined by measuring this resistance. In the method of the present application, there is no restriction on the diameters of electrodes. The sheet materials in the present application may be monolayer or multilayer of metal materials, alloy materials, semiconductor materials, coating materials, and films, which may be stand-alone or be supported by non-conductive substrates.

The thickness of the sheet material of the present application is much less than the diameter of the electrodes. Therefore, in the present application, it is considered that the potential and electric current in the sheet material generated when direct current passes through the circular electrode pair are uniform in the depth direction of the material, and the theoretical analysis thereof can be treated mathematically as a two-dimensional problem. The planar dimensions of the sheet material are much greater than the distance between the electrodes, and the closest distance between each electrode and the edge of the material is much greater than the distance between the electrodes. Therefore, the potential and electric current at the edge of the material are very small and the edge reflection effect can be neglected.

Further, in the present application, it is required that the conductivity of the electrode material be much greater than the conductivity of the sheet material. Therefore, potential distributions within each of the electrodes is considered to be uniform, and it is required that the contact resistance of the electrode/sheet material interface be small. That is, as compared with the resistance of the sheet material, the resistance of the electrode and the contact resistance of the electrode/sheet material interface are small, thus being negligible in the test. Similarly, the resistance of the electrode lead is known or considered to be very small (see FIG. 1) in the measurement. Therefore, during the theoretical analysis, the resistance within the electrode, the resistance of the electrode lead, and the contact resistance of the electrode/substrate interface are not taken into account.

In the present application, the electrode refers to the connection means between the sheet material and the circuit, including pressure-bonding (such as a probe), gluing, soldering, electric welding, and other connection methods.

The study found that when taking the connection line between the centers of the two electrodes as the x-axis, and the left electrode A (i.e., the first electrode 2 on the left in FIG. 1) as being connected to the negative electrode of the DC power supply and the right electrode B (i.e., the second electrode 3 on the right in FIG. 1) as being connected to the positive electrode, the potential distribution V (x, y) in the sheet material outside the electrode can be calculated according to equation (1) in FIG. 3.

Herein, $I_0$ is the DC current flowing between the two electrodes through the sheet material, and $R_\square = \rho/t$ is the sheet resistance of the sheet material, wherein $\rho$ and t are the resistivity and the thickness of the sheet material, respectively. $\pi = 3.1416$ is the constant of pi.

$L_A$ and $L_B$ are the distances between each of the two common points of electrodes and the center of electrode A, which are determined by equations (2) and (3) in FIG. 3.

Herein, $r_A$ and $r_B$ are the radii of electrode A and electrode B respectively, and $L_{AB}$ is the distance between the centers of the two electrodes (see FIG. 1 and FIG. 2), whose centers are positioned on the x-axis at $-(L_A+L_B)/2$ and $L_{AB}-(L_A+L_B)/2$, respectively.

The corresponding current density vector in the sheet material is calculated by equation (4) in FIG. 3.

Herein, i and j are unit vectors in x-axis and y-axis directions, respectively.

It was found by the inventor that equation (1) also indicates the potential field generated by the two point electrodes in the sheet material. FIG. 2 shows the potential (equation (1)) and the current (equation (4)) fields in sheet material generated by direct current from the two point electrodes on the x-axis, which are located at $(L_A/2-L_B/2, 0)$ and $(L_B/2-L_A/2, 0)$, respectively. The theoretical analysis shows that the potential and current fields in the sheet material outside the electrodes are the same as those generated in the sheet material by the two point electrodes (with the same amount of current) at the common points of the electrodes. The solid circles around the point electrodes represent the equipotential lines, and their radii are 0.5 $L_0$, 0.25 $L_0$, 0.1 $L_0$ 0.05 $L_0$, and 0.01 $L_0$, respectively, in descending order. Herein, $L_0$ is the distance between the two common point electrodes (i.e., the two common electrodes), and $L_0 = L_B - L_A$. The larger the equipotential circle is, the farther the center of the circle deviates from the point electrode. The positions of the centers of the equipotential circles can be calculated according to equations (2) and (3). In FIG. 2, the dotted lines represent the current lines in the sheet, representing the paths of the currents that are emitted at angles in steps of 15° from the two point electrode positions. The density of the dotted lines represents the current intensity in the sheet material. The inset at the top right corner of FIG. 2 shows the detailed distribution of the electric potential and the current in vicinity of the right point electrode, indicating that the center of the equipotential circles close to the point electrode deviates decreasingly from the point electrode, and the angular distribution of current intensity close to the point electrode is highly uniform. According to equations (2) and (3), the center of the left equipotential circle is positioned at $-(L_A+L_B)/2$ and the center of the right equipotential line is positioned at $L_{AB}-(L_A+L_B)/2$ on the x-axis, where LAB is the distance between the two centers of the equipotential circles corresponding to the edge contours of the electrodes.

It was found by the inventor that the electric potential and current fields generated by two circular electrodes in a sheet material (excluding the parts covered by the electrodes) are the same as those generated by two point electrodes with the same direct current passing through in the sheet material. For example, when the size and position of the left electrode is same as those of the equipotential circle with a radius of 0.1 $L_0$ and the size and position of the right electrode is same as those of the equipotential circle with a radius of 0.25 $L_0$, the same potential and current fields will be produced in the sheet material (excluding the parts covered by the electrodes) as those produced by two point electrodes (with the same current passing through) located at the common point positions of the electrodes.

It was found by the inventor that the current path in the material between the circular electrodes is a circular arc passing through the two point electrodes, which can be described by equation (5) in FIG. 3.

Herein, $\theta$ is the angle between the current line passing through the left point electrode and the x-axis. The center of the arc is positioned at $-L_0/)2\tan\theta)$ on the y-axis, and the radius of the arc is $|L_0(2\sin\theta)|$.

From the previous theoretical finding, the resistance of the sheet material between the two electrodes can be calculated according to equation (6) in FIG. 3.

By experimentally measuring the resistance KO in the material between the two electrodes, the sheet resistance of the sheet material can be calculated from the measured resistance according to equation (7) in FIG. 3.

The potential and current fields in the sheet material depend on the radii of the two circular electrodes, the distance between the electrodes, and the passing current. In an ideal case, the current in the sheet material is generated from the circular edge of the electrode, and the central area of the circular electrode does not participate in the transmission of current, and the properties of the sheet material covered by the electrode do not affect the measurement. Therefore, it is possible to use circular electrodes to cover particular flaw (including voids, contamination, uneven thickness, etc.) areas in the sheet material. From this it is further deduced that an annular electrode works as effectively as the circular electrode in the measurement, and also the use of annular electrodes may be able to improve the contact between the electrode edges and the sheet material.

In summary, by using the testing method for sheet resistance of sheet material in the present application, the difficulties existing in the prior art can be overcome, the limitation on the electrode diameter can be removed, and the contact resistance of electrode/substrate interface and the electric heating effect on the sample surface can be reduced by increasing the electrode diameter.

The invention can be embodied in many forms without departing from the essential natures of the application, and the embodiments of the application are intended to be illustrative and not restrictive. The scope of the invention is defined by the claims rather than the specification, and all modifications which fall within the scope of the claims, or equivalents of the scope of the invention, are to be included in the claims.

The invention claimed is:

1. A testing method for sheet resistance of a sheet material, comprising:
   mounting two circular or annular electrodes on a surface of the sheet material, the two circular or annular electrodes comprising a first electrode and a second electrode;
   measuring a resistance between the first electrode and the second electrode; and
   calculating the sheet resistance of the sheet material on the basis of the following equation:

$$R_\Box = \frac{2\pi R_{AB}}{\ln\left[\frac{L_{AB}^2 - r_A^2 - r_B^2}{2r_A r_B} + \sqrt{\left(\frac{L_{AB}^2 - r_A^2 - r_B^2}{2r_A r_B}\right)^2 - 1}\right]}$$

wherein, $R_{AB}$ is the resistance measured between the first electrode and the second electrode, $r_A$ and $r_B$ are radii of the first electrode and the second electrode respectively, and L is a distance between centers of the first electrode and the second electrode.

2. The testing method according to claim 1, wherein the sheet material is a conductive material, including metal material, alloy material, semiconductor material, coating, or film material.

3. The testing method according to claim 1, wherein the sheet material includes monolayer material or multilayer material, and the sheet material is stand-alone or supported by a non-conductive substrate.

4. The testing method according to claim 1, wherein the first electrode and the second electrode are connection means between the sheet material and a circuit, and the first electrode and the second electrode are connected to the sheet material by pressure-contact, gluing, soldering, or electric welding of the surface of the sheet material.

5. The testing method according to claim 1,
wherein a thickness of the sheet material is uniform; and
wherein the thickness of the sheet material is much less than diameters of the first electrode and the second electrode.

6. The testing method according to claim 1,
wherein planar dimensions of the sheet material are much greater than the distance between centers of the first electrode and the second electrode; and
wherein the planar dimensions are a length, a width, or a diameter of the sheet material.

7. The testing method according to claim 1,
wherein the distance between the first electrode or the second electrode and an edge of the sheet material is much greater than the distance between the centers of the first electrode and the second electrode.

8. The testing method according to claim 1,
wherein a point source model is configured to be used to calculate a potential and current fields in the sheet material generated by the two circular or annular electrodes.

9. The testing method according to claim 5,
wherein the thickness of the sheet material has an unevenness of less than 1%.

10. The testing method according to claim 5,
wherein the thickness of the sheet material is less than 1/10 of a smaller diameter of the first electrode and the second electrode.

11. The testing method according to claim 6,
wherein the planar dimensions of the sheet material are greater than 10 times the distance between the centers of the first electrode and the second electrode.

12. The testing method according to claim 7,
wherein the distance between the first electrode or the second electrode and the edge of the sheet material is greater than 5 times the distance between the centers of the first electrode and the second electrode.

* * * * *